United States Patent [19]
Drane

[11] Patent Number: 5,377,681
[45] Date of Patent: Jan. 3, 1995

[54] METHOD OF DIAGNOSING IMPAIRED BLOOD FLOW

[75] Inventor: Walter E. Drane, Gainesville, Fla.

[73] Assignee: University of Florida, Gainesville, Fla.

[21] Appl. No.: 242,708

[22] Filed: May 13, 1994

Related U.S. Application Data

[63] Continuation of Ser. No. 899,227, Jun. 16, 1992, abandoned, which is a continuation of Ser. No. 434,336, Nov. 13, 1989, abandoned.

[51] Int. Cl.$^6$ ............................. A61B 5/05; A61B 6/00
[52] U.S. Cl. .................................. 128/653.4; 128/654
[58] Field of Search ............................. 424/1.11, 4, 9; 128/653.4, 654

[56] References Cited

U.S. PATENT DOCUMENTS

| | | | |
|---|---|---|---|
| 4,598,368 | 7/1986 | Umemura | 358/111 X |
| 4,615,876 | 10/1986 | Troutner et al. | 424/1.1 |
| 4,705,849 | 11/1987 | Nunn et al. | 534/14 |
| 4,710,875 | 12/1987 | Nakajima et al. | 364/414 |
| 4,729,379 | 3/1988 | Ohe | 128/654 |
| 4,746,507 | 3/1988 | Quag | 424/9 |
| 4,862,359 | 8/1989 | Trivedi et al. | 364/413.05 |
| 4,917,880 | 4/1990 | Wretlind et al. | 424/5 |
| 4,931,270 | 6/1990 | Horn et al. | 424/1.1 |
| 4,989,142 | 1/1991 | Crawford | 364/413.15 |
| 5,046,499 | 9/1991 | Berger | 128/654 |
| 5,055,288 | 10/1991 | Lewis et al. | 424/9 |
| 5,150,427 | 9/1992 | Frazee et al. | 382/48 |

FOREIGN PATENT DOCUMENTS

| | | | |
|---|---|---|---|
| 2020945 | 11/1979 | United Kingdom | 358/111 |

OTHER PUBLICATIONS

Posterboard 1130: Zielonka et al. Multicenter clinical trial of 99m-Tc teboroxime (SQ30,217; Cardiotec) as a myocardial perfusion agent. J Nucl Med 1989; 30: 1745.

Bellinger R et al. Multicenter trial of Tc-99m Teboroxime: A new Myocardial perfusion imaging agent. Presentation #106, 425.

Pohost GM et al. Thallium Redistribution: Mechanisms and Clinical utility. Seminars in Nuclear Medicine 1980; X: 70.

Pohost GM et al. Differentiation of transiently ischemic from infarcted myocardium by serial imaging after a single dose of thallium-201. Circulation 1977; 294–302.

Beller GA, et al. Time course of Thallium-201 redistribution after transient myocardial ischemia. Circulation 1980; 61: 791.

Okada RD. Kinetics of Thallium-201 in Reperfused canine myocardium after coronary artery occlusion. JACC 1984; 3: 1245-1251.

Pohost GM et al. Thallium Redistribution in dogs with severe coronary artery stenosis of fixed caliber. Circulation Research 1981; 439.

Beller GA. Role of Myocardial Perfusion Imaging in Evaluating thrombolytic therapy for acute myocardial infarction. JACC 1987; 9: 661-668.

Gewirtz H, et al. The effect of ischemia on thallium-201 clearance from the myocardium. Circulation 1979; 58: 215-219.

Maseri A, et al. Transient transmural reduction of myocardial blood flow, demonstrated by thallium-201 scintigraphy, as a cause of variant angina. Circulation 1976; 54: 280-288.

Kruger et al., "A Digital Video Image Processor for Real-Time X-Ray Subtraction Imaging", Optical Engineering, vol. 17, No. 6 (1978) pp. 652-655.

Fleming, "Technique for contralateral subtraction in lateral lung radionuclide imaging," Medical & Biological Engineering & Computing, vol. 17 (1979) pp. 751-756.

*Primary Examiner*—Robert L. Stoll
*Assistant Examiner*—Lara E. Chapman
*Attorney, Agent, or Firm*—Pettis & McDonald

[57] ABSTRACT

A method of diagnosing impaired blood flow to an organ. The method is especially useful in patients which cannot undergo stress testing due to risk factors.

54 Claims, 4 Drawing Sheets

METHOD OF DIAGNOSING IMPAIRED BLOOD FLOW

This is a continuation of application Ser. No. 07/899,277 filed Jun. 16, 1992, now abandoned, which application is a continuation of application Serial No. 07/434,336, filed on Nov. 13, 1989, now abandoned.

BACKGROUND OF THE INVENTION

1. FIELD OF THE INVENTION

The present invention relates to a method of diagnosing impaired blood flow in an organ using in vivo imaging.

2. DESCRIPTION OF RELATED ART

In recent years the use of various contrast agents for non-invasive diagnostic imaging has become routine. In parallel with this increased use has come improvements in both the quality and diversity of instruments used for detection, as well as the development of new contrast agents for use with these various instruments. The search for the ideal agents for use in diagnostic imaging has focused on agents with static distribution where uptake is relative to some functional parameter such as blood flow, metabolic rate, or receptor density. Static biodistribution is particularly important when the diagnostic instrument is based on single photon emission computed tomography (SPECT), since the vast majority of SPECT imaging devices require about 20–30 minutes for image acquisition, during which time little change in contrast agent distribution can occur. Consequently, agents that lack a static distribution have been systematically discarded for measuring regional blood perfusion. This is particularly true of technetium or iodine radiolabeled compounds for measurement of blood flow in the heart or the brain.

Present tests for diagnostic imaging which measure regional organ perfusion can be divided into three broad categories: those which are based upon the administration of a contrast agent which is distributed relative to blood flow, without further change; those based upon the administration of an inert gas; and those based upon the administration of positron-labelled physiological radiotracers.

The use of contrast agents which are distributed relative to blood flow in the absence of further change, such as $^{99m}$Tc-HMPAO (hexamethyl propyleneamine oxime) for brain imaging and $^{99m}$Tc-isonitriles for myocardial imaging, have significant draw-backs. For example, when asymmetries occur, it is difficult to distinguish between areas of potentially increased blood flow and areas of decreased blood flow. As a consequence, it is difficult to discern whether one area is increased or whether the adjacent area is decreased.

The use of inert gas also presents significant difficulties. The typically utilized gas, xenon, is difficult to administer and imaging with this agent provides very limited spatial resolution. In addition, this technique has never been shown to be capable of detecting coronary artery disease at rest.

The administration of positron-labelled physiological radiotracers as contrast agents, such as $^{13}$N-ammonia or $^{15}$O-water, require on-site cyclotron production and radiochemical preparation and can only be imaged using a positron emission tomograph (PET) scanner which is not available in many nuclear medicine laboratories. This technique has also never been shown to be capable of detecting coronary artery disease at rest.

One area where there has been considerable interest in the use of contrast agents has been for the detection of coronary artery disease using myocardial perfusion scintigraphy. At the present time the primary agent used for such diagnosis is $^{201}$thallous chloride. Unfortunately, this agent presents significant disadvantages in that it has a long physical half-life, poor imaging characteristics, complicated biokinetics in the heart, and high cost. Another group of agents which are used, the isonitriles, do not redistribute, that is, show a relative increase in regional myocardial concentration in a lesion from the images recorded initially to the images recorded later, and require separate stress and rest injections over at least a 4 hour period.

A major drawback associated with many of the agents presently used is that they require exercise stress testing for the detection of coronary artery disease thereby creating a situation which is potentially dangerous to patients with cardiac disease. As a consequence, such agents can only be used at a limited level with patients recovering from acute myocardial infarction. In addition, many patients, such as those recovering from major surgery, or are handicapped, cannot exercise adequately to undergo the stress testing regimen.

A group of drugs which has been of interest in the area of myocardial perfusion scintigraphy are the boronic acid adducts of technetium dioxime, or BATO agents (U.S. Pat. Nos. 4,705,849; 4,714,605). However, it had been believed that even these agents required testing under conditions of stress and non-stress. (Seldin, et al., *The Journal of Nuclear Medicine*, 30:312, 1989).

Consequently, a considerable need exists for a method of evaluating impaired blood flow in an organ of a patient which will allow the patient to remain at rest, which can be performed in a shorter period of time, and which requires only one injection of the contrast agent.

SUMMARY OF THE INVENTION

Recognizing the role that non-invasive diagnostics imaging can play in the diagnosis of impaired organ blood flow and the severe limitations associated with existing protocols, the inventors studied various ways that such imaging could be performed. These efforts have culminated in the development of a method which is extremely accurate and specific in diagnosing impaired organ blood flow using in vivo imaging technology.

The method which was developed utilizes a non-inert radionuclide which, surprisingly, can be performed on a patient at rest thereby obviating the prior art requirement of diagnosis under stress conditions. As a consequence, the method of the invention requires only one injection, can be performed in less than one hour, and results in a significant cost savings.

DESCRIPTION OF THE PREFERRED EMBODIMENTS

Figure 1:
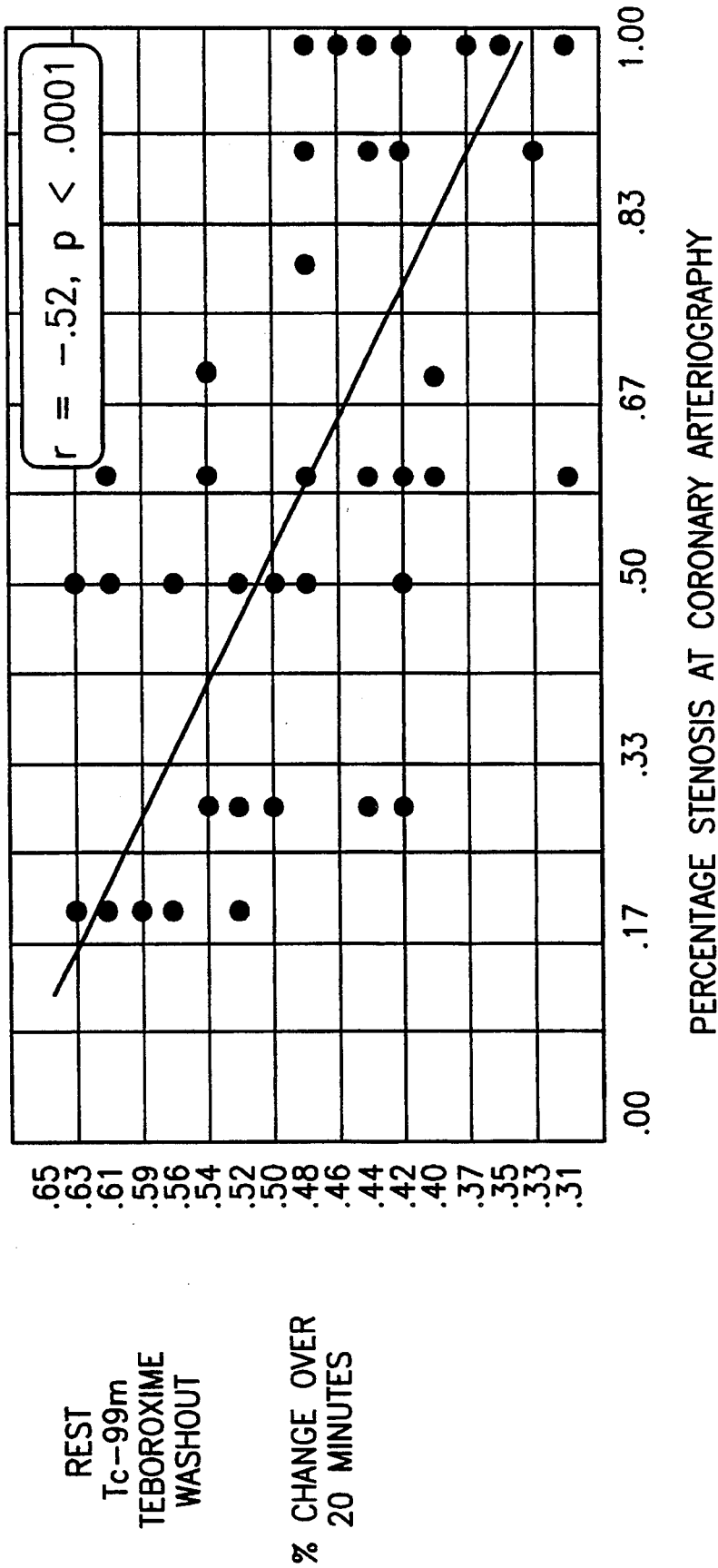
FIG. 1: Graphical illustration of the relationship between $^{99m}$Tc-teboroxime washout rate and degree of coronary artery disease.

The present invention relates to a novel method for detecting impaired blood flow in an organ of a patient which can be performed while the patient is at rest. By eliminating the need for stress testing, which is required by existing methodologies, the method of the invention can be used on many patients which heretofore had been precluded from in vivo diagnostic testing by perfusion imaging. For example, patients with coronary artery disease, chronic lung disease, peripheral vascular disease, or orthopedic problems.

In its most basic form, the invention provides a method of diagnosing impaired blood flow in an organ of a patient at rest which comprises:
   a. administering a diagnostically effective amount of non-inert contrast agent to the patient;
   b. generating a first series of images of the contrast agent in the organ at a time after administration sufficient for the contrast agent to be extracted to the organ;
   c. generating a second series of images of the contrast agent in the organ at a time after the first series of images sufficient to allow for a detectable decrease of contrast agent in the organ to occur; and
   d. displaying the generated first and second series of images.

Interpretation of the diagnostic results obtained by use of the present invention is significantly improved by the use of a novel image enhancement and presentation method. The novel method involves processing the dynamic image data such that a single resultant image graphically indicates the condition of the scanned organ. This processing method can be used for both at rest and under stress diagnosis.

Further, while it is preferred to process the data to obtain a tomographic image, it should be noted that it is possible to use the method of the invention to obtain data expressed as a planar image for purposes of diagnosis of impaired blood flow to the organ.

The image enhancement and presentation method includes the following initial steps:
  1. The initial data for the organ being studied is acquired and reconstructions of each primary image plane are generated.

For example, in one of the illustrated embodiments discussed below in conjunction with Example 1, SPECT imaging was begun using a multi-headed SPECT device. Initial SPECT data acquisitions were obtained over 360° using a step-and-shoot mode with a three-head SPECT device, with each head covering 120° of the 360° acquisition (20 stops at 6° intervals at 5 secs/stop). Serial 2-minute tomograms were performed for a total time of 20 minutes, resulting in the acquisition of data for 10 sequential primary images. Data acquisition and reconstruction of the data into the primary tomographic images were performed in known fashion using a 64×64 data matrix. The tomographic reconstruction was performed using a backprojection technique. The image data may be filtered in known fashion, if desired. In the embodiment shown in Example 1, a Hamming filter (0.7 frequency cut-off) was utilized for all scans. If desired, the image data may also be corrected for attenuation of the gamma ray emissions of the body.

2. After reconstruction of the primary transverse image planes, the image data may be reoriented and one or more secondary images constructed in known fashion along one or more desired axes of the organ being studied, in order to focus on particular aspects of interest in the organ.

For example, when studying the heart, the image data may be reoriented about the long axis of the heart, since the long axis of the heart is typically not perpendicular to the transverse scanning planes used to acquire the data to reconstruct the primary image planes. A set of secondary images "slices" may be constructed parallel to the XY, XZ, and YZ planes relative to the X, Y, and Z axes of the reoriented heart image data. Often of particular interest are secondary image slices constructed along the short axis of the heart, through the left ventricle (LV). A slice thickness of $\approx 1.5$ cm is utilized for each secondary image in the embodiment shown in Example 1 (although other thicknesses may be used, if desired). The number of secondary image slices so reconstructed may be varied as desired; four slices were constructed for each time sequence in the embodiment shown in Example 1.

Figure 2:
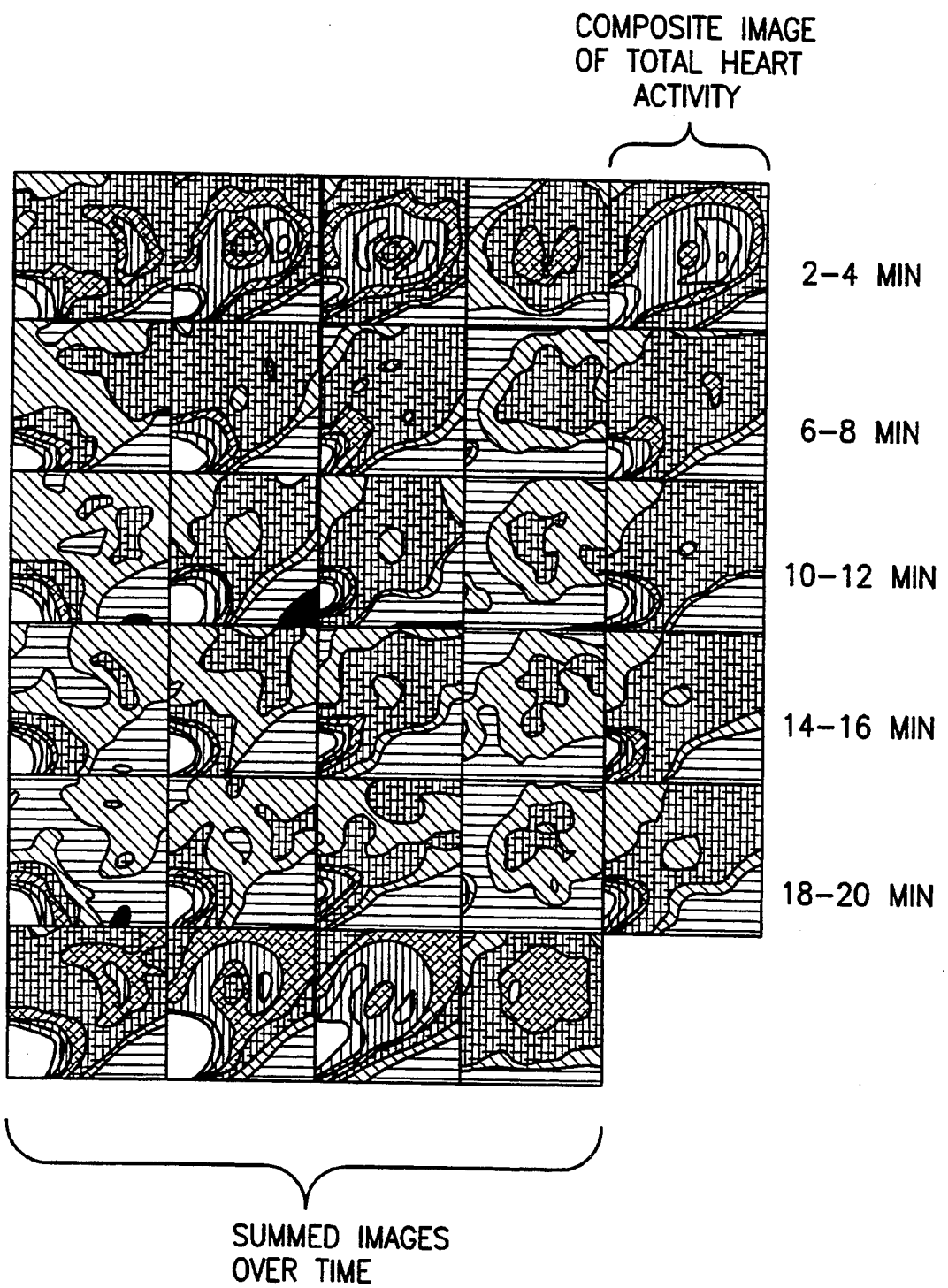
FIG. 2: A drawing of a photograph of several tomographic images.

FIG. 2 shows a photographic montage of the spatial and time sequences of a series of such constructed secondary image slices. The first four images in each row represent four spatially separated slices of an organ (in this case, the heart, along its short axis through the left ventricle). The first five images in each column represent the same secondary image slice taken at different time intervals (as labeled along the right side of the images).

Although diagnosis could be made based upon images such as those shown in rows 1–5 and columns 1–4 of FIG. 2, it has been found that further image processing produces a single image that more graphically indicates the condition of the scanned organ. Therefore, the inventive image enhancement and presentation method includes the following further steps:
  3. An image which is called a "parametric washout composite image" in the inventive method is created and displayed. In the preferred embodiment of the method, the following process is used:
    (a) All images from a first time period comprising a series of spatially separated secondary image slices along a chosen axis are added together, on a pixel by pixel basis, to form a "first composite" image.

For instance, in Example 1 set forth below, all of the short axis images from a first time period (such as the 2–4 minute dynamic SPECT series of the first row shown in FIG. 2) are added to form a "first composite" image of the whole heart. An example of such a composite image is shown in the fifth column of the first row in FIG. 2.

(b) All images from a second time period comprising a series of spatially separated secondary image slices along a chosen axis are added together, on a pixel by pixel basis, to form a "second composite" image.

For instance, in Example 1 set forth below, all of the short axis images from a second time period (such as the 18–20 minute dynamic SPECT series of the fifth row shown in FIG. 2) are added to form a "second composite" image of the whole heart. An example of such a composite image is shown in the fifth column of the fifth row in FIG. 2.

(c) The "first composite" image is subtracted from the "second composite" image on a pixel by pixel basis. This creates a "degree of washout image".

(d) The degree-of-washout image may then be further processed for display to show globally reduced washout. This is done in the preferred embodiment by assigning the maximum display color/gray scale value to the areas of maximum washout on the degree-of-washout image, with the remaining display scale values being assigned in sequence to the values of the remaining image areas, forming a non-normalized image. Next, without altering the display scale, the pixels in the non-normalized image are multiplied by a constant, the fraction of whole organ washout (see paragraph below). This manipulation creates a normalized parametric washout composite image (which may then be transferred to film) that permits detection of diffuse (global) symmetrical reduction in perfusion by showing globally reduced washout. Since uniform reduction in blood flow is rare to the entire heart or brain, the normalized image is frequently not necessary for interpretation.

The fraction of whole organ washout is calculated by first determining the counts per pixel in one or more regions of interest in the organ in the images of the first time period, which indicates the amount of maximal uptake of contrast agent. Then the counts per pixel in the regions of interest are determined in the images of the second time period, which indicates the amount of washout of the contrast agent. The second count value is subtracted from the first count value, and the result is divided by the first count value, to give the percentage of washout of contrast agent from the organ.

For example, in Example 1 set forth below, the count activity at 18-20 minutes is subtracted from the count activity at 2-4 minutes, and the result is divided by the count activity at 2-4 minutes. If, for example, there is a 50% washout from the whole heart at 18-20 minutes, then the fraction is 0.50. Thus, to create the final parametric washout composite image from the non-normalized image, each pixel is multiplied by 0.50.

Figure 3A:
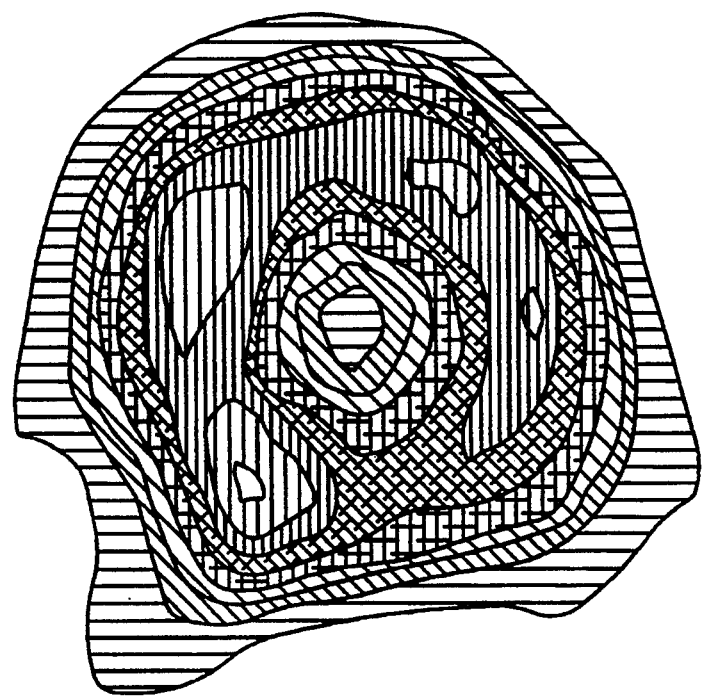
FIG. 3: A drawing of a photograph of a parametric washout composite image of a normal organ with FIG. 3a representing the washout in a patient at rest.
FIG. 3b represents the washout in a patient under a stress test.
Figure 3B:
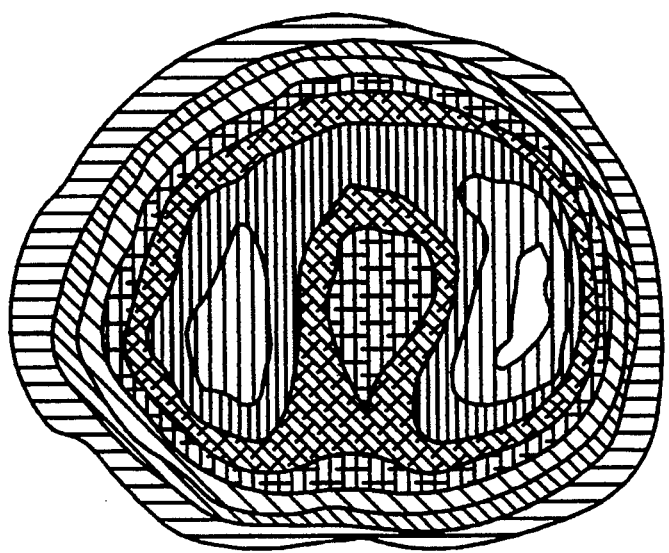
Figure 4:
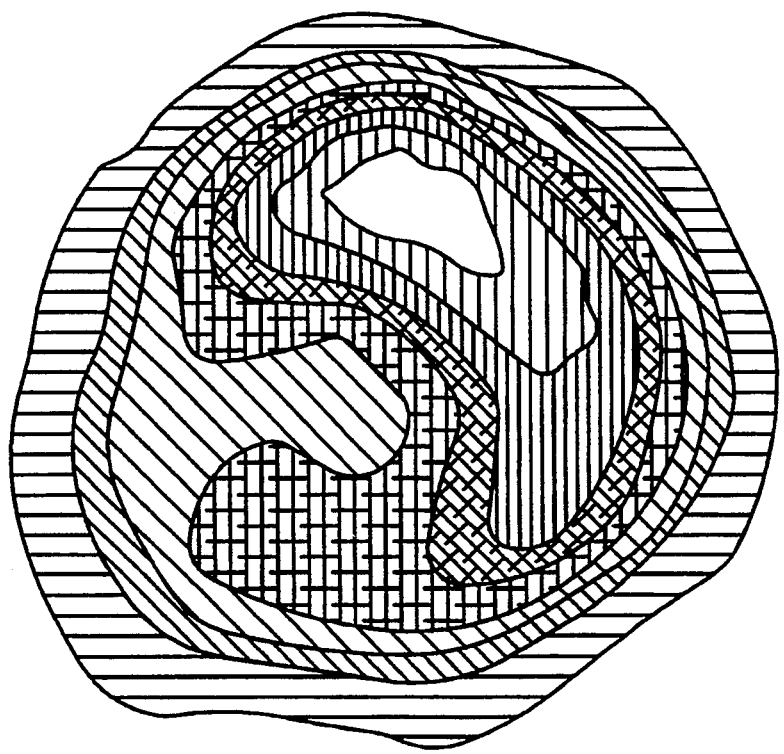
FIG. 4: A drawing of a photograph of a parametric washout composite image of organ with impaired blood flow.

Examples of the application of the novel image enhancement and presentation method are shown in FIGS. 3 and 4, which are photographs of several parametric washout composite images. FIG. 3 shows a parametric washout composite image for a subject having a normal left ventricle, indicated by a central area of uniform intensity. FIG. 4 shows a parametric washout composite image for a subject having an abnormal left anterior descending artery and circumflex arteries, indicated by the yellow areas of the heart where washout of the contrast agent has been delayed.

The parametric washout composite images allow an interpreter to achieve a high specificity of diagnosis of organ condition. Ordinary tomographic images (such as those shown in rows 1-5 and columns 1-4 of FIG. 2) are subject to a fairly high degree of "false positive" readings. Use of a parametric washout composite image substantially reduces the incidence of false positive interpretations (see also Table 1 below, and the related discussion). The inventive image enhancement and presentation method thus has great value in diagnosis of organ condition.

It should be noted that parametric washout composite images alone cannot be used for complete diagnosis, since they do not differentiate infarct from ischemia. One or more of the series of ordinary tomographic images is necessary to make such a distinction.

Comparison of the early scans vs. the late scans reveals areas of relatively delayed washout at sites in the organ supplied by diseased or damaged arteries. As a consequence, areas of the organ with normal arteries washout fast, while areas supplied by diseased arteries washout more slowly. A parametric image of washout is assembled by creating a two-dimensional representation of the early activity, then creating a two-dimensional representation of the late activity, and subtracting the latter from the former. The resulting image is a two-dimensional representation of washout of the agent from the entire organ in regard to degree of washout over the time difference between the early and late image acquisitions. Thus, the image displays the areas of abnormal washout in the organ in a single image. In the case of images of the heart, a review of the early vs. late scans differentiates myocardial infarct from ischemia. Myocardial infarct shows decreased uptake on both early and late scans, while ischemia shows a defect on the early scan that shows a relative increase in activity on the late scan.

In the method of the invention, the first series of measurements are performed at a time following administration of the contrast agent sufficient for the organ of interest to have extracted a sufficient quantity of the agent to be detectable in the instrument being used. This time will vary depending upon such factors as the age and condition of the patient, the contrast imaging agent which is utilized, and the particular instruments which is being used to form the image composite. These same factors will influence the time at which the second series of measurements are performed taking also into account that the delay in performing the second series of measurements should be sufficient such that the particular instrument being used can accurately detect a drop in detectability of the contrast imaging agent as compared to the signal measured in the first series of measurements. This delay is desirable so that when the second series of measurements are subtracted from the first series of measurements, a clear and accurate composite image related to washout of the imaging agent can be compiled.

In using the method of the invention for the in vivo diagnosis of impaired blood flow to an organ the contrast agent is given in a dose which is diagnostically effective. The term "diagnostically effective" means that the amount of contrast agent is administered in sufficient quantity to enable its detection in the organ of interest at the initial series of measurements to a degree that a statistically significant drop in the level of detection of the contrast agent occurs by the time the second series of measurements is acquired. In so doing, this concentration of contrast agent will permit a meaningful measurement of washout to allow for the discrimination of the regions within the organ which display impaired blood flow due to decreased ability of the organ to wash the contrast agent out of the impaired region of the organ.

The contrast agent which is selected will depend upon the nature of the instrument which is used. Thus, SPECT and PET instruments will typically utilize a radionuclide contrast agent, whereas MRI and CT instruments will typically utilize a non-radionuclide contrast agent. The contrast agent chosen must have a type of signal which is detectable for a given type of instrument. In the method of the invention SPECT, CT, PET, and MRI are preferred instruments for visualizing the diagnostic image.

Typically, when a radionuclide contrast agent is used in conjunction with a SPECT instrument, it is administered at a dose of from about 1 to about 100 mCi, preferably from about 20 to about 40 mCi, most preferably from about 30 to about 40 mCi. PET radionuclide contrast agents are typically administered from about 1 to about 300 mCi, preferably from about 20 to about 100 mCi, most preferably from about 30 to about 70 mCi. MRI contrast agents are typically administered at a dose of from about 1 to about 60 grams, preferably from about 2 to about 30 grams, most preferably from about 5 to 10 grams. CT contrast agents are typically administered at a dose of from about 5 to about 100 grams, preferably from about 10 to about 80 grams, most preferably from about 30 to about 60 grams. Regardless of whether a radionuclide or non-radionuclide contrast agent is utilized, the dose level is readily ascertainable by one of skill in the art without undue experimentation.

The method of the invention can be used to diagnose impaired blood flow in any organ assessable to the contrast imaging agent, such as the brain and heart. The method is particularly advantageous when used in imaging the heart by allowing the measurement of myocardial perfusion at rest, without the need for stress exercise which is normally used to increase the imaging differences between normal and ischemic myocardium. Because the determination of the rate of washout does not require an absolute quantitation of peak uptake of an administered contrast agent, the method of the invention has greater quantitative accuracy than a method which attempts to quantitate the absolute uptake using a static agent.

The identification of patients presenting with a reduction of normal blood flow (ischemia) to an organ in the body is clinically very important, especially if regional localization is achieved. The method of the invention allows the detection of regional localization of areas of reduced blood flow on an intra-organal basis when used with a pharmaceutical that has high extraction and subsequent washout from the organ in question. The method of the invention can be applied through other imaging modalities, including computerized tomography (CT), using complex pharmaceuticals which alter tissue attenuation, or using magnetic resonance imaging (MRI), using contrast agents that alter the organ magnetic signal.

When applied to myocardial perfusion studies, the method of the invention can be used for screening coronary artery disease, testing the effectiveness of coronary artery bypass grafting, evaluating the effectiveness of coronary artery angioplasty, and determining the effects of various drugs on coronary perfusion.

Cerebral measurements using the method of the invention hold promise in being able to diagnose such important clinical conditions as the diagnosis of acute stroke and differentiation of large-vessel infarcts from lacunar infarcts, determining prognosis after acute stroke (If anatomic damage equals perfusion damage, then function is non-recoverable. If anatomic damage is less than perfusion damage, then function is potentially recoverable.) The differentiation of various causes of dementia (particularly to differentiate Alzheimer's disease from multi-infarct dementia), localization of abnormal areas in the brain causing focal epilepsy, detection of vasospasm after subarachnoid hemorrhage, and determine the effectiveness of drugs or procedures intended to improve cerebral perfusion.

Typically, the first set of measurements will be performed from about 10 seconds to about 30 minutes, preferably from about 30 seconds to about 20 minutes, most preferably from about 1 minute to about 15 minutes, after administration of the contrast agent.

The second set of measurements will typically be performed from about 10 minutes to about 200 minutes, preferably from about 15 minutes to about 100 minutes, most preferably from about 17 to about 80 minutes, after administration of the contrast agent.

In the case of radionuclide contrast agents, an important factor in selecting a radionuclide for in vivo diagnosis is that the half-life of the radionuclide be long enough so that it is still detectable at the time of maximum uptake by the target, but short enough so that deleterious radiation with respect to the host is minimized. Ideally, a radionuclide used for in vivo imaging will lack a particle emission, but produce a large number of photons in the 140–200 keV range, which may be readily detected by conventional gamma cameras.

Of major importance is the biokinetics of the contrast agent. It is highly preferred that the contrast agent used in the method of the invention exhibit high organ extraction and rapid organ washout in the absence of significant wash back to the organ.

Elements which are particularly useful in magnetic resonance imaging (MRI), are paramagnetic isotopes which include $^{157}$Gd, $^{55}$Mn, $^{162}$Dy, $^{52}$Cr, and $^{56}$Fe. CT contrast agents typically are iodinated and can be ionic, such as Conray®, or non-ionic, such as Isovue®. Contrast agents typically used in PET instruments include $^{11}$C, $^{13}$N, $^{15}$O, and $^{18}$F. Those of skill in the art will know of numerous other contrast agents, or can readily identify them, without undue experimentation.

Agents which are particularly preferred in the method of the invention are those which can be used in SPECT instruments. Especially preferred are boronic acid addicts of technetium oxime complexes (Nunn, et al., *Journal of Nuclear Medicine*, 27:893, 1986) such as $^{99m}$Tc-teboroxime.

The above disclosure generally describes the present invention. A further understanding can be obtained by reference to the following specific examples which are provided for purposes of illustration only and are not intended to be limiting unless otherwise specified.

EXAMPLE 1

DETECTION OF CORONARY ARTERY DISEASE

A. PATIENT POPULATION SELECTION AND TESTING

A study was done using a population consisting of 10 patients suspected of having coronary artery disease and 5 normal volunteers. The 10 patients all presented with angina (mean age: 59 years; range: 41–76 years). The 5 normal volunteers were all young asymptomatic males (mean age: 26 years; range: 21–31 years). All normal volunteers had normal stress electrocardiograms and normal stress thallium examinations.

Each patient underwent stress electrocardiographic examination, using upright treadmill exercise (standard Bruce protocol). At 15–30 seconds prior to peak exercise, each patient was administered a 15–20 mCi dose of $^{99m}$Tc-teboroxime intravenously. With a 2 minute delay to move the patient from treadmill to SPECT imaging table, SPECT imaging was begun using a TRIAD® multi-headed SPECT device. 360° SPECT acquisitions were performed in step-and-shoot mode, with each head covering 120° of the 360° acquisition (20 stops at 6° intervals for 5 sec/stop). Non-circular orbit was used and camera orbit was programmed prior to stress examination for each individual. Initial camera rotation was counter-clockwise, and the direction of rotation reversed on each of the sequential tomographic acquisitions. Serial 2 minute tomograms were performed for a total time of 20 minutes, resulting in 10 sequential tomographic acquisitions. Acquisition and reconstruction were performed in a 64×64 matrix. Tomographic reconstruction was performed using a filtered backprojection technique, without attenuation correction. A Hamming filter (0.7 frequency cut-off) was utilized for all scans. After transverse reconstruction, reorientation was performed along the long axis of the heart and images were made in the short, vertical, and horizontal axes. A slice thickness of ≈1.5 cm was utilized.

Using a similar acquisition sequence, a separate resting study was performed at 90–180 minutes after the stress study. This delay was to allow the patient to return to the "resting" physiologic state, as well to allow the interval clearance from the myocardium of the previously administered radiotracer dose. Imaging was begun 2 minutes after the intravenous administration of ≈30–35 mCi of $^{99m}$Tc-teboroxime.

Washout analysis was performed for both the stress and the rest $^{99m}$Tc-teboroxime dynamic SPECT series. Each tomographic study was reformatted into 4 short axes slices and a "dynamic imaging matrix" was created. Twelve regions-of-interest (ROI's) were placed on each tomographic study (upper slice at mitral valve plane: anterior, lateral, and posterior; next two left ventricular slices: anterior, lateral, posterior, and septal; apical slice: single region covering the apex). These ROI's were applied to each corresponding slice from the entire sequence of dynamic tomographic images. Because of the short time of dynamic acquisition, decay-correction was not performed. ROI activity was determined as counts/pixel. Quantitative data was analyzed in regard to percentage of maximal uptake and in regard to percentage washout at 20 minutes by subtracting the activity at 18–20 minutes from the activity at 2–4 minutes and then dividing this value by the activity at 2–4 minutes.

Using dynamic region-of-interest analysis, a variable sized ROI was applied to the entire left ventricle (LV) in short axis presentation. This "volumetric" or "3-D" count analysis was applied to the dynamic series with calculation of the "whole heart washout curve" and the "whole heart percentage washout at 20 minutes".

Parametric washout images were created using the image enhancement and presentation method described above. The result is a single parametric washout composite image, such as is shown photographically in FIGS. 3 and 4.

The following imaging combinations of 99mTC-teboroxime scans were analyzed for the presence or absence of evidence of coronary artery disease:

a) stress 2–4 minute scan vs. rest 2–4 minute scan (standard method of analysis),
b) stress 2–4 minute scan vs. stress 18–20 minute scan,
c) rest 2–4 minute scan vs. rest 18–20 minute scan.

At separate interpretation, both the stress and the rest parametric "washout" images were interpreted for signs of ischemic heart disease, as indicated by a regional decrease in washout amplitude.

All scans were interpreted by two blinded, independent investigators where each set of images or each image type was interpreted separately. Any disagreements were settled by joint interpretation and consensus. (Blinded interpretation was in agreement in 14 of the 15 cases, without need for joint interpretation.)

The scans were interpreted by the following classification system:

Normal No evidence of disease.
Ischemic Characterized by a decrease in myocardial uptake early after stress on the stress/rest combination (or a decrease on the early image of the early/late combination at either stress or rest) which "fills in" on rest imaging (or on the late scans for the early/late combinations).
Infarcted Characterized by a decrease in myocardial uptake seen on both the stress/rest or the early/late imaging combinations.
Mixed Characterized by a decrease in myocardial uptake early after stress on the stress/rest combination (or a decrease on the early image of the early/late combination at either stress or rest) which only partially "fills in" on rest imaging (or on the late scans for the early/late combination—some defect still observable.
Equivocal Unable to diagnose.

At the time of interpretation of each imaging set, an attempt at prediction of the diseased coronary artery-(ies) was made for each of the major vascular territories: (left anterior descending artery, circumflex artery, right coronary artery).

All 10 patients underwent coronary arteriography (single-plane analysis) using standard technique. Visual analysis of percentage stenosis was performed, using ≦50% stenosis as definition of significant disease. This method is the clinical "standard of care" for the diagnosis of coronary artery disease.

The $^{99m}$Tc-teboroxime imaging results were correlated with the results of coronary arteriography (the simple presence/absence of disease and the percentage stenosis). Correlation of the $^{99m}$Tc-teboroxime results with the overall clinical impression of the presence or absence of disease was also performed. Correlative and linear regression analysis was performed between percentage stenosis at coronary arteriography and the quantitative parameters of $^{99m}$Tc-teboroxime uptake and washout. For the purposes of correlation, the left anterior descending artery was assumed to supply the anterior and septal walls, as well as the apex. The right coronary artery was assumed to supply the inferior/posterior basal wall, and the circumflex artery was assumed to supply the lateral wall.

B. RESULTS

Of the 10 patients suspected of having coronary artery disease, 9 had significant disease at coronary arteriography. $^{99m}$Tc-teboroxime scans were abnormal in all 9 of these patients (preliminary sensitivity =100%). Of the 6 individuals without significant disease (1 patient with "normal" coronary arteries at catheterization and 5 normal volunteers), the $^{99m}$Tc-teboroxime imaging combinations were normal in 4 of 6 patients (67% preliminary specificity). However, in the patients with potentially "false-positive" scans, the parametric "washout" images showed normal washout in the areas of suspected abnormality and prevented their misinterpretation. Interpretation of each imaging combination is shown in Table 1.

TABLE 1

| Test Condition | Without parametric washout image | | With parametric washout image | |
| --- | --- | --- | --- | --- |
| | Sensitivity | Specificity | Sensitivity | Specificity |
| stress 2–4 min/ rest 2–4 min | 9 of 9 (100%) | 4 of 6 (67%) | 9 of 9 (100%) | 6 of 6 (100%) |
| stress 2–4 min/ stress 18–20 min | 9 of 9 (100%) | 4 of 6 (67%) | 9 of 9 (100%) | 6 of 6 (100%) |
| rest 2–4 min/ rest 18–20 min | 9 of 9 (100%) | 3 of 6 (50%) | 9 of 9 (100%) | 6 of 6 (100%) |

The parametric images allow the interpreter to achieve a high specificity. These images alone cannot be used to differentiate infarct vs. ischemia. One of the series of imaging combinations is necessary for this latter definition.

$99m$Tc-teboroxime washout rates showed a moderate, but highly statistically significant correlation with percentage stenosis. In the 10 patients who underwent coronary arteriography, percentage stenosis in diseased arteries was compared to the 20 minute percentage washout of $^{99m}$Tc-teboroxime at both stress and rest. The normal arteries were not analyzed, since a "normal" interpretation at catheterization gives no indication of flow or caliber of the vessel. This analysis revealed a correlation coefficient (r) of $-0.59$ ($p<0.0001$) for stress washout and a correlation coefficient (r) of $-0.52$ ($p<0.0001$) for rest washout. As shown in FIG. 1, this data indicates that a correlation exists between the washout rate of $^{99m}$Tc-teboroxime and the degree of coronary artery disease.

This "moderate" correlation between percentage stenosis and washout rates of $^{99m}$Tc-teboroxime is more significant than appears at face-value. This correlation was tested in its worst-case scenario, because of the following facts:

(1) Visual analysis of percentage stenosis of a coronary artery on arteriography is an imprecise measure, with at least 10–15% error. This would only serve to falsely lower the measured correlation between percentage stenosis and $^{99m}$Tc-teboroxime washout.

(2) Washout analysis was correlated with percentage stenosis over the entire area of potentially abnormal myocardium. If the lesion is distal, only a portion of this area would have abnormal washout. This assumption only serves to falsely lower the measured correlation between percentage stenosis and $^{99m}$Tc-teboroxime washout.

(3) The "standard" vascular anatomy was assumed in all individuals. Variation in arterial blood supply to the heart would only serve to falsely lower the measured correlation between percentage stenosis and $^{99m}$Tc-teboroxime washout.

As such, the true correlation between coronary artery disease and washout analysis of $^{99m}$Tc-teboroxime distribution at either stress or rest is likely much higher than reported above.

EXAMPLE 2

ANALYSIS OF CEREBRAL PERFUSION

A. PATIENT POPULATION

The study population consisted of 10 volunteers (mean age: 30 years) who had normal Magnetic Resonance Imaging (MRI) scans of their brains and normal neurological examinations prior to entry into the study.

Each volunteer was positioned supine on the TRIAD ® imager, and an intravenous catheter was inserted. After a 5–10 minute delay for the pain of catheter insertion to subside, the volunteer was injected with 15–20 mCi of $^{99m}$Tc-teboroxime. After waiting 30 seconds for delivery to the brain, serial dynamic SPECT acquisitions were performed. 360° SPECT acquisitions were performed in step-and-shoot mode, with each head covering 120° of the 360° acquisition (40 stops at 3° intervals for 20 sec/stop). Non-circular orbit was used. Initial camera rotation was counter-clockwise, and the direction of rotation reversed on each of the sequential tomographic acquisitions. Serial 15 minute tomograms were performed for a total time of 75 minutes, resulting in 5 sequential tomographic acquisitions. Acquisition and reconstruction were performed in a $128 \times 128$ matrix. Tomographic reconstruction was performed using a filtered backprojection technique, with attenuation correction (standard method of Chang). A Hamming filter (0.7 frequency cut-off) was utilized for all scans. After transverse reconstruction, reorientation was performed along the vertical and horizontal axes.

An image of "washout" was created by subtracting the 60–75 minute scan from the 0–15 minute scan. The resultant "washout" image was interpreted in regard to its display of the pattern of "normal" cerebral perfusion and compared in this regard with the serial tomographs of the distribution.

B. Results

A pattern of "normal" cerebral perfusion was produced by the parametric washout images of $^{99m}$Tc-teboroxime. The distribution images of $^{99m}$Tc-teboroxime over time did not display the same degree of resolution and similarity to normal cerebral perfusion. These latter images are also degraded by background activity in the soft-tissues surrounding the brain, which is eliminated on the "washout" images.

These images are quantatible. An area with increased flow will show increased uptake on the initial 0–15 minute $^{99m}$Tc-teboroxime scans and also on the parametric washout image. If this area were instead normal, and in fact, all other areas of the brain had decreased flow, the initial 0–15 minute scan would be unchanged, but the parametric washout image would show a normal percentage washout in this area, with diminished washout throughout the reminder of the brain. This method of washout analysis would also allow the detection of global changes in cerebral perfusion. Percentage washout of an agent like $^{99m}$Tc-teboroxime using dynamic SPECT can be correlated with actual blood flow measurements from xenon-CT, radioxenon imaging, or PET imaging over a range of normal and abnormal blood flows. A "look-up" table can be created allowing extrapolation of cerebral blood flow in milliliters/minute/gram of tissue for any given percentage washout of radiotracer.

The invention now being fully described, it will be apparent to one of ordinary skill in the art that many changes and modifications can be made without departing from the spirit or scope of the invention.

I claim:

1. A method of diagnosing impaired blood flow in an organ of a patient which comprises:
   a. administering a diagnostically effective amount of non-inert contrast agent to the patient;
   b. generating a first series of generally parallel two-dimensional images, spatially separated along one axis of major blood supply to said organ, of the contrast agent in the organ at a first time after administration sufficient for the contrast agent to be extracted to the organ, said first series of said two-dimensional spatially separated images forming a three-dimensional representation of the contrast agent uptake of said organ as of said first time;
   c. adding together, on a pixel by pixel basis, substantially all images from said first series, thereby generating a two-dimensional first composite image from the first series of two-dimensional spatially separated images, such that said first composite image represents an image of total contrast agent uptake as of said first time for the organ of interest, oriented along said one axis;
   d. generating a second series of generally parallel two-dimensional images, spatially separated along said one axis, of the contrast agent in the organ at a second time after said first series of images sufficient to allow for a detectable decrease of contrast agent in the organ to occur, said second series of two-dimensional spatially separated images forming a three-dimensional representation of the contrast agent retention by the organ of interest as of said second time;
   e. adding together, on a pixel by pixel basis, substantially all images from said second series, thereby generating a two-dimensional second composite image from said second series of two-dimensional spatially separated images, such that said second composite image represents an image of the total contrast agent retention for the organ of interest, as of said second time and oriented along said axis;
   f. generating a two-dimensional third composite image by subtracting said two-dimensional second composite image from said two-dimensional first composite image to determine the degree of decrease of contrast agent from the organ, said third composite image representing an image of total contrast agent washout between said first time and said second time, indicating the status of the arterial blood supply along said axis; and
   g. displaying the two-dimensional third composite image.

2. A method of diagnosing impaired blood flow in an organ of a patient at rest which comprises:
   a. administering a diagnostically effective amount of non-inert contrast agent to the at-rest patient;
   b. generating a first series of generally parallel two-dimensional images, spatially separated along one axis of major blood supply to said organ, of the contrast agent in the organ at a time after administration sufficient for the contrast agent to be extracted to the organ, said first series of two-dimensional spatially separated images forming a three-dimensional representation of the contrast agent uptake by the organ as of said first time;
   c. adding together, on a pixel by pixel basis, substantially all images from said first series, thereby generating a two-dimensional first composite image from said first series of two-dimensional spatially separated images such that said first composite image represents an image of total at-rest contrast agent uptake by said organ as of said first time for said organ and oriented along said one axis;
   d. generating a second series of generally parallel two-dimensional images, spatially separated along said one axis, of the contrast agent in the organ at a second time after said first series of images sufficient to allow for a detectable decrease of said contrast agent in the organ to occur, said second series of two-dimensional spatially separated images forming a three-dimensional representation of the contrast agent retention of said organ of interest as of said second time;
   e. adding together, on a pixel by pixel basis, substantially all images from said second series, thereby generating a two-dimensional second composite image from said second series of two-dimensional spatially separated images, such that said second composite image represents an image of total contrast agent retention for said organ of interest as of said second time and oriented along said one axis;
   f. generating a two-dimensional third composite image by subtracting said two-dimensional second composite image from said two-dimensional first composite image to determine the degree of decrease of contrast agent from the organ, said third composite image representing an image of total contrast agent washout between said first time and said second time, indicating the status of at-rest arterial blood supply of just said organ of interest and oriented along said one axis of major blood supply; and
   g. displaying the two-dimensional third composite image.

3. The method of claim 2, further including the steps of:
   a. after generating the third composite image, assigning a first of a series of display scale values to the areas of maximum decrease of contrast agent from the organ on the third composite image, with the remaining display scale values being assigned in sequence to the values of any remaining areas of the third composite image, to form a non-normalized composite image; and
   b. multiplying each picture element of the non-normalized image by a constant, comprising the quantity of whole organ decrease of contrast agent from the organ, to form a normalized composite image.

4. A method of diagnosing coronary artery disease in a patient at rest which comprises:
   a. administering a diagnostically effective amount of non-inert contrast agent to the at-rest patient;
   b. generating a first series of generally parallel two-dimensional images, spatially separated along one axis of major blood supply, of the contrast agent in the heart of the at-rest patient at a first time after administration sufficient for the contrast agent to be extracted to the heart, said first series of two-dimensional spatially separated images forming a three-dimensional representation of resting blood flow to the heart of said patient;
   c. adding together, on a pixel by pixel basis, substantially all images from said first series, thereby generating a two-dimensional first composite image from said first series of two-dimensional spatially separated images, said first composite image representing an image of total contrast agent retention for just the heart as of said first time and oriented along said one axis of major blood supply;

d. generating a second series of two-dimensional images, spatially separated along said one axis of major blood supply, of the contrast agent in said heart at a time after said first series of images sufficient to allow for a detectable decrease of contrast agent in the heart to occur, said second series of two-dimensional spatially separated images forming a three-dimensional representation of contrast agent retention as of said second time in the heart;

e. adding together, on a pixel by pixel basis, substantially all images from said second series, thereby generating a two-dimensional second composite image from said second series of two-dimensional spatially separated images, said second composite image representing an image of total contrast agent retention for just the heart as of said second time and oriented along said axis of major blood supply;

f. generating a two-dimensional third composite image by subtracting said two-dimensional second composite image from said two-dimensional first composite image to determine the degree of decrease of contrast agent from the heart, said third composite image representing an image of total contrast agent washout, indicating the status of coronary arteries of the heart, oriented along the axis of major blood supply; and g. displaying the two-dimensional third composite image.

5. The method as in any of claims 1, 2, or 4, wherein the contrast agent is used in a CT instrument.

6. The method of claim 5, wherein the contrast agent is selected from the group consisting of ionic and non-ionic iodinated contrast agents.

7. The method of claim 6, wherein the contrast agent is selected from the group consisting of iothalamate sodium and iopamidol.

8. The method as in any of claims 1, 2, or 4, wherein the contrast agent is used in a PET instrument.

9. The method of claim 8, wherein the contrast agent is selected from the group consisting of $^{11}C$, $^{13}N$, $^{15}O$, and $^{18}F$.

10. The method as in any of claims 1, 2, or 4, wherein the contrast agent is used in an MRI instrument.

11. The method of claim 10, wherein the contrast agent is selected from the group consisting of $^{157}Gd$, $^{55}Mn$, $^{162}Dy$, $^{52}Cr$, and $^{56}Fe$.

12. The method as in any of claims 1, 2, or 4, wherein the contrast agent is used in a SPECT instrument.

13. The method of claim 12, wherein the contrast agent is a boronic acid adduct of technetium dioxime.

14. The method of claim 13, wherein the boronic acid adduct of the technetium dioxime is $^{99m}Tc$-teboroxime.

15. The method as in either of claims 1 or 2, wherein the organ diagnosed is selected from the group consisting of the heart and the brain.

16. The method as in either of claims 1 or 2, wherein the first series of images are generated from about 10 seconds to about 30 minutes after administration of the contrast agent.

17. The method as in either of claims 1 or 2, wherein the first series of images are generated from about 30 seconds to about 20 minutes after administration of the contrast agent.

18. The method as in either of claims 1 or 2, wherein the first series of images are generated from about 1 minute to about 15 minutes after administration of the contrast agent.

19. The method as in either of claims 1 or 2, wherein the second series of images are generated from about 12 minutes to about 200 minutes after administration of the contrast agent.

20. The method as in either of claims 1 or 2, wherein the second series of images are generated from about 15 minutes to about 100 minutes after administration of the contrast agent.

21. The method as in either of claims 1 or 2, wherein the second series of images are generated from about 17 to about 80 minutes after administration of the contrast agent.

22. The method of claim 5, wherein the contrast agent is administered from about 5 to about 100 grams.

23. The method of claim 5, wherein the contrast agent is administered from about 10 to about 80 grams.

24. The method of claim 5, wherein the contrast agent is administered from about 30 to about 60 grams.

25. The method of claim 8, wherein the contrast agent is administered from about 1 to about 300 mCi.

26. The method of claim 8, wherein the contrast agent is administered from about 20 to about 100 mCi.

27. The method of claim 8, wherein the contrast agent is administered from about 30 to about 70 mCi.

28. The method of claim 10, wherein the contrast agent is administered from about 1 to about 60 grams.

29. The method of claim 10, wherein the contrast agent is administered from about 2 to about 30 grams.

30. The method of claim 10, wherein the contrast agent is administered from about 5 to about 10 grams.

31. The method of claim 12, wherein the contrast agent is administered from about 10 to about 100 mCi.

32. The method of claim 12, wherein the contrast agent is administered from about 20 to about 40 mCi.

33. The method of claim 12, wherein the contrast agent is administered from about 30 to about 40 mCi.

34. The method as in any of claims 1, 2, or 4, wherein the first and second images are tomographic images.

35. The method of claims 1, 2, or 4, wherein the contrast agent is administered intravenously.

36. The method as in any of claims 1, 2, or 4, wherein the contrast agent is used in a gamma camera instrument.

37. A method of diagnosing coronary artery disease in a patient at rest, comprising the steps of a. administering intravenously a diagnostically effective amount of a contrast agent to said at-rest patient;

b. generating a first series of two-dimensional images of said contrast agent in the myocardium of said patient at a first time after administration sufficient for said contrast agent to be extracted to said myocardium, said images being spatially separated along one axis of major blood supply, said first series of two-dimensional spatially separated images forming a three-dimensional representation of contrast agent uptake in the myocardium as of said first time;

c. adding together, on a pixel by pixel basis, substantially all of said two-dimensional images from said first series, whereby is generated a two-dimensional first composite image from said first series of two-dimensional spatially separated images, said first composite image representing an image of total contrast agent uptake for just the myocardium, as of said first time and oriented along said one axis of major blood flow;

d. generating a second series of two-dimensional images of said myocardium of said patient at a second time after said first series of images sufficient to allow for a detectable decrease of said contrast agent in said myocardium, said second series of images being spatially separated along said one axis, said second series of images forming a three-dimensional representation of the contrast agent retention in the myocardium of said contrast agent as of said second time;

e. adding together, on a pixel by pixel basis, substantially all of said two-dimensional images from said second series, whereby is generated a two-dimensional second composite image from said second series of two-dimensional spatially separated images, said second composite image representing an image of total contrast agent retention for just the myocardium, as of said second time and oriented along said one axis of major blood supply;

f. comparing said first image with said second image to evaluate the degree of decrease of said contrast agent in said myocardium of said patient by generating a two-dimensional third composite image by subtracting said second composite image from said first composite image to determine the degree of decrease of said contrast agent from said myocardium, said third composite image representing an image of total washout of said contrast agent from the myocardium between said first time and said second time, thereby indicating the status of blood flow in the coronary arteries of the heart, oriented along said one axis of major blood supply; and g. displaying said two-dimensional third composite image.

38. The method of claim 37 further comprising the steps of a. after generating said third composite image, assigning a first of a series of display scale values to the areas of maximum decrease of said contrast agent from said myocardium on said third composite image, with the remaining said display scale values being assigned in sequence to the values of any remaining areas of said third composite image, to form a non-normalized composite image; and b. multiplying each picture element of the non-normalized image by a constant, comprising the quantity of decrease throughout the entire said myocardium of said contrast agent, to form a normalized composite image.

39. The method of claim 37 wherein the images are formed using a computerized tomography instrument.

40. The method of claim 39 wherein the contrast agent is selected from the group consisting of ionic and non-ionic iodinated contrast agents.

41. The method of claim 40 wherein the contrast agent is selected from the group consisting of Conray ® and Isovue ®.

42. The method of claim 37 wherein the image is formed by the use of a PET instrument.

43. The method of claim 42 wherein said contrast agent is selected from the group consisting of $^{11}C$, $^{13}N$, $^{15}O$, and $^{18}F$.

44. The method of claim 37 wherein the image is formed by the use of an MRI instrument.

45. The method of claim 43 wherein said contrast agent is selected from the group consisting of $^{157}Gd$, $^{55}Mn$, $^{162}Dy$, $^{52}Cr$ and $^{56}Fe$.

46. The method as in claim 37 wherein the image is formed by the use of a SPECT instrument.

47. The method of claim 46 wherein the contrast agent is a boronic acid adduct of technetium dioxime.

48. The method of claim 47 wherein the boronic acid adduct of the technetium dioxime is $^{99m}Tc$-teboroxime.

49. The method of claim 37 wherein the first series of images are generated from about 10 seconds to about 30 minutes after administration of the contrast agent.

50. The method of claim 37 wherein the first series of images are generated from about 30 seconds to about 20 minutes after administration of the contrast agent.

51. The method of claim 37 wherein the first series of images are generated from about 1 minute to about 15 minutes after administration of the contrast agent.

52. The method of claim 37 wherein the second series of images are generated from about 12 minutes to about 200 minutes after administration of the contrast agent.

53. The method of claim 37 wherein the second series of images are generated from about 15 minutes to about 100 minutes after administration of the contrast agent.

54. The method of claim 37 wherein the second series of images are generated from about 17 to about 80 minutes after administration of the contrast agent.

* * * * *